United States Patent
Bonhoeffer et al.

(10) Patent No.: US 9,949,824 B2
(45) Date of Patent: *Apr. 24, 2018

(54) DEVICES USEFUL FOR IMPLANTATION AT A HEART VALVE

(71) Applicants: JENAVALVE TECHNOLOGY, INC., Irvine, CA (US); MEDTRONIC VASCULAR GALWAY LIMITED, Santa Rosa, CA (US)

(72) Inventors: Philipp Bonhoeffer, London (GB); Younes Boudjemline, Clamart (FR)

(73) Assignees: JENAVALVE TECHNOLOGY, INC., Irvine, CA (US); MEDTRONIC VASCULAR GALWAY LIMITED, Galway (IE)

( * ) Notice: Subject to any disclaimer, the term of this patent is extended or adjusted under 35 U.S.C. 154(b) by 279 days.

This patent is subject to a terminal disclaimer.

(21) Appl. No.: 14/576,344

(22) Filed: Dec. 19, 2014

(65) Prior Publication Data

US 2015/0105857 A1    Apr. 16, 2015

Related U.S. Application Data

(63) Continuation of application No. 14/019,071, filed on Sep. 5, 2013, now abandoned, which is a continuation
(Continued)

(30) Foreign Application Priority Data

Aug. 3, 2001   (FR) ...................................... 01 10444

(51) Int. Cl.
   *A61F 2/24*    (2006.01)
   *A61F 2/06*    (2013.01)

(52) U.S. Cl.
   CPC .......... *A61F 2/2409* (2013.01); *A61F 2/2418* (2013.01); *A61F 2/2427* (2013.01);
   (Continued)

(58) Field of Classification Search
   CPC ........ A61F 2/24; A61F 2/2409; A61F 2/2418; A61F 2/2427; A61F 2/243; A61F 2/2436; A61F 2/2439; A61F 2250/001
   See application file for complete search history.

(56) References Cited

U.S. PATENT DOCUMENTS

| 4,950,227 A | 8/1990 | Savin et al. |
| 5,002,566 A | 3/1991 | Carpentier et al. |

(Continued)

FOREIGN PATENT DOCUMENTS

| AT | 11792 U1 | 5/2011 |
| AT | 547068 T | 3/2012 |

(Continued)

OTHER PUBLICATIONS

Aortenklappenbioprothese erfolgreich in der Entwicklung, (1 page) May 16, 2003.

(Continued)

*Primary Examiner* — Ryan J Severson

(57) ABSTRACT

A device useful for implantation at a native heart valve can include an anchor element having a tubular configuration defining a longitudinal direction and a circumference, a heart valve prosthesis disposed within the anchor element, and a plurality of elongate members positioned at equidistant angular intervals about the circumference of the anchor element. The device can be configured to be transitioned from a radially collapsed delivery configuration to a radially expanded implantation configuration, and the plurality of
(Continued)

elongate members can have a length extending in the longitudinal direction of the tubular member in the expanded implantation configuration.

22 Claims, 7 Drawing Sheets

Related U.S. Application Data of application No. 13/279,800, filed on Oct. 24, 2011, now Pat. No. 8,585,756, which is a continuation of application No. 12/138,983, filed on Jun. 13, 2008, now Pat. No. 8,216,301, which is a continuation of application No. 10/210,085, filed on Aug. 2, 2002, now abandoned.

(52) U.S. Cl.
CPC ...... *A61F 2/2436* (2013.01); *A61F 2002/061* (2013.01); *A61F 2230/0054* (2013.01); *A61F 2250/001* (2013.01)

(56) References Cited

U.S. PATENT DOCUMENTS

| | | | |
|---|---|---|---|
| 5,053,008 A | 10/1991 | Bajaj |
| 5,061,277 A | 10/1991 | Carpentier et al. |
| 5,094,661 A | 3/1992 | Levy et al. |
| 5,104,407 A | 4/1992 | Lam et al. |
| 5,197,979 A | 3/1993 | Quintero et al. |
| 5,279,612 A | 1/1994 | Eberhardt |
| 5,332,402 A | 7/1994 | Teitelbaum |
| 5,336,258 A | 8/1994 | Quintero et al. |
| 5,344,427 A | 9/1994 | Cottenceau et al. |
| 5,352,240 A | 10/1994 | Ross |
| 5,368,608 A | 11/1994 | Levy et al. |
| 5,411,552 A | 5/1995 | Andersen et al. |
| 5,456,713 A | 10/1995 | Chuter |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,063 A | 10/1998 | Cox |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,855,601 A | 1/1999 | Bessler et al. |
| 5,868,783 A | 2/1999 | Tower |
| 5,876,434 A | 3/1999 | Flomenblit et al. |
| 5,880,242 A | 3/1999 | Hu et al. |
| 5,899,936 A | 5/1999 | Goldstein |
| 5,928,281 A | 7/1999 | Huynh et al. |
| 5,935,163 A | 8/1999 | Gabbay |
| 5,104,407 B1 | 9/1999 | Lam et al. |
| 5,954,764 A | 9/1999 | Parodi |
| 5,976,178 A | 11/1999 | Goldsteen et al. |
| 6,001,126 A | 12/1999 | Nguyen-Thien-Nhon |
| 5,061,277 B1 | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,458,153 B1 | 10/2002 | Bailey et al. |
| 6,471,723 B1 | 10/2002 | Ashworth et al. |
| 6,478,819 B2 | 11/2002 | Moe |
| 6,485,524 B2 | 11/2002 | Strecker |
| 6,503,272 B2 | 1/2003 | Duerig et al. |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,551,303 B1 | 4/2003 | Van Tassel et al. |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,137,184 B2 | 11/2006 | Schreck |
| 7,141,064 B2 | 11/2006 | Scott et al. |
| 7,163,556 B2 | 1/2007 | Xie et al. |
| 7,189,259 B2 | 3/2007 | Simionescu et al. |
| 7,195,641 B2 | 3/2007 | Palmaz et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,241,257 B1 | 7/2007 | Ainsworth et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 7,704,222 B2 | 4/2010 | Wilk et al. |
| 7,736,327 B2 | 6/2010 | Wilk et al. |
| 7,803,185 B2 | 9/2010 | Gabbay |

(56) References Cited

U.S. PATENT DOCUMENTS

| | | |
|---|---|---|
| 7,896,913 B2 | 3/2011 | Damm et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,579,965 B2 | 11/2013 | Bonhoeffer et al. |
| 8,585,756 B2 | 11/2013 | Bonhoeffer et al. |
| 2001/0011187 A1 | 8/2001 | Pavcnik et al. |
| 2001/0039450 A1 | 11/2001 | Pavcnik et al. |
| 2002/0007138 A1 | 1/2002 | Wilk et al. |
| 2002/0032481 A1 | 3/2002 | Gabbay |
| 2002/0055775 A1 | 5/2002 | Carpentier et al. |
| 2002/0123790 A1 | 9/2002 | White et al. |
| 2002/0133226 A1 | 9/2002 | Marquez et al. |
| 2002/0151970 A1 | 10/2002 | Garrison et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0210301 A1 | 10/2004 | Obermiller et al. |
| 2004/0210304 A1 | 10/2004 | Seguin et al. |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1 | 4/2005 | Rowe |
| 2005/0075776 A1 | 4/2005 | Cho |
| 2005/0096726 A1 | 5/2005 | Sequin et al. |
| 2005/0096736 A1 | 5/2005 | Osse et al. |
| 2005/0098547 A1 | 5/2005 | Cali et al. |
| 2005/0113910 A1 | 5/2005 | Paniagua et al. |
| 2005/0119728 A1 | 6/2005 | Sarac |
| 2005/0119736 A1 | 6/2005 | Zilla et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0111770 A1 | 5/2006 | Pavcnik et al. |
| 2006/0142846 A1 | 6/2006 | Pavcnik et al. |
| 2006/0149360 A1 | 7/2006 | Schwammenthal et al. |
| 2006/0167543 A1 | 7/2006 | Bailey et al. |
| 2006/0193885 A1 | 8/2006 | Neethling et al. |
| 2006/0210597 A1 | 9/2006 | Hiles |
| 2006/0229718 A1 | 10/2006 | Marquez |
| 2006/0229719 A1 | 10/2006 | Marquez et al. |
| 2006/0246584 A1 | 11/2006 | Covelli |
| 2006/0259134 A1 | 11/2006 | Schwammenthal et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Hans-Reiner et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Hans-Reiner et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0203576 A1 | 8/2007 | Lee et al. |
| 2007/0213813 A1 | 9/2007 | Von Segesser et al. |
| 2007/0239271 A1 | 10/2007 | Nguyen |
| 2007/0244551 A1 | 10/2007 | Stobie |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0133003 A1 | 6/2008 | Seguin et al. |
| 2008/0140189 A1 | 6/2008 | Nguyen et al. |
| 2008/0154355 A1 | 6/2008 | Benichou et al. |
| 2008/0200977 A1 | 8/2008 | Paul et al. |
| 2008/0215143 A1 | 9/2008 | Seguin |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0054968 A1 | 2/2009 | Bonhoeffer et al. |
| 2009/0062908 A1 | 3/2009 | Bonhoeffer et al. |
| 2010/0070027 A1 | 3/2010 | Bonhoeffer et al. |
| 2010/0210991 A1 | 8/2010 | Wilk et al. |
| 2011/0034852 A1 | 2/2011 | Häusler et al. |
| 2012/0209374 A1 | 8/2012 | Bonhoeffer et al. |

(56) References Cited

U.S. PATENT DOCUMENTS

| | | | |
|---|---|---|---|
| 2012/0283823 A1 | 11/2012 | Bonhoeffer et al. | |
| 2014/0012370 A1 | 1/2014 | Bonhoeffer et al. | |
| 2015/0094804 A1 | 4/2015 | Bonhoeffer et al. | |

FOREIGN PATENT DOCUMENTS

| | | |
|---|---|---|
| CA | 2436258 A1 | 1/2005 |
| CA | 2848485 A1 | 1/2005 |
| CA | 2848490 A1 | 1/2005 |
| DE | 19546692 A1 | 6/1997 |
| DE | 20003874 U1 | 5/2000 |
| DE | 19857887 A1 | 6/2000 |
| DE | 10010073 A1 | 9/2001 |
| DE | 10010074 A1 | 10/2001 |
| DE | 101 21 210 A1 | 11/2002 |
| DE | 19546692 C2 | 11/2002 |
| DE | 10010074 B4 | 4/2005 |
| DE | 19857887 B4 | 5/2005 |
| DE | 10010073 B4 | 12/2005 |
| DE | 20221871 U1 | 9/2008 |
| DE | 69937568 T2 | 9/2008 |
| DK | 1112042 T3 | 2/2008 |
| DK | 200800058 U1 | 6/2008 |
| DK | 200800058 U3 | 7/2008 |
| DK | 1259195 T3 | 2/2009 |
| DK | 1281375 T3 | 5/2012 |
| EP | 0084395 A1 | 7/1983 |
| EP | 0458877 | 8/1990 |
| EP | 0402036 B1 | 12/1990 |
| EP | 0402176 B1 | 12/1990 |
| EP | 0458877 B1 | 4/1991 |
| EP | 0515324 A1 | 11/1992 |
| EP | 0547135 B1 | 6/1993 |
| EP | 0871414 | 9/1995 |
| EP | 0 592 410 B1 | 10/1995 |
| EP | 0756498 | 10/1995 |
| EP | 0 592 410 B1 | 11/1995 |
| EP | 0786970 | 5/1996 |
| EP | 0729364 B1 | 9/1996 |
| EP | 0756498 B1 | 5/1997 |
| EP | 0778775 B1 | 6/1997 |
| EP | 0786970 | 8/1997 |
| EP | 0888142 | 9/1997 |
| EP | 0971649 | 10/1998 |
| EP | 0928615 A1 | 7/1999 |
| EP | 1051204 | 7/1999 |
| EP | 1089676 | 12/1999 |
| EP | 0986348 B1 | 3/2000 |
| EP | 1117446 | 4/2000 |
| EP | 1 164 976 | 8/2000 |
| EP | 1158937 | 9/2000 |
| EP | 1 251 805 B1 | 10/2000 |
| EP | 1041942 B1 | 10/2000 |
| EP | 1041943 B1 | 10/2000 |
| EP | 1171061 | 10/2000 |
| EP | 1206179 | 2/2001 |
| EP | 1 233 731 | 5/2001 |
| EP | 1112042 A1 | 7/2001 |
| EP | 1117446 B1 | 7/2001 |
| EP | 1 255 510 | 8/2001 |
| EP | 1259193 | 9/2001 |
| EP | 1 233 731 B1 | 5/2002 |
| EP | 1 330 213 | 5/2002 |
| EP | 1206179 B1 | 5/2002 |
| EP | 1347785 | 8/2002 |
| EP | 1235537 | 9/2002 |
| EP | 1248655 | 10/2002 |
| EP | 1251804 B1 | 10/2002 |
| EP | 1257305 | 11/2002 |
| EP | 1259195 | 11/2002 |
| EP | 0 971 649 B1 | 12/2002 |
| EP | 1395208 | 12/2002 |
| EP | 1 401 359 | 1/2003 |
| EP | 1406561 | 1/2003 |
| EP | 1281357 A2 | 2/2003 |
| EP | 1281375 A2 | 2/2003 |
| EP | 1408882 | 2/2003 |
| EP | 1 435 878 | 4/2003 |
| EP | 1 435 879 | 4/2003 |
| EP | 1 441 672 | 6/2003 |
| EP | 1 017 868 B1 | 9/2003 |
| EP | 1354569 A1 | 10/2003 |
| EP | 1494616 | 10/2003 |
| EP | 1281375 A3 | 12/2003 |
| EP | 1 519 697 | 1/2004 |
| EP | 1 539 047 | 4/2004 |
| EP | 1551274 | 4/2004 |
| EP | 1 560 542 | 5/2004 |
| EP | 1414295 | 5/2004 |
| EP | 1 603 493 | 9/2004 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1 663 070 | 3/2005 |
| EP | 1 253 875 B1 | 4/2005 |
| EP | 1 667 614 | 4/2005 |
| EP | 1 251 803 B1 | 6/2005 |
| EP | 1 702 247 | 7/2005 |
| EP | 1734902 | 8/2005 |
| EP | 1614400 A2 | 1/2006 |
| EP | 1835948 | 6/2006 |
| EP | 1863545 | 9/2006 |
| EP | 1893132 | 11/2006 |
| EP | 1901681 | 12/2006 |
| EP | 1 255 510 B1 | 3/2007 |
| EP | 1835948 | 9/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1886649 A3 | 4/2008 |
| EP | 1259195 B1 | 10/2008 |
| EP | 1994913 A2 | 11/2008 |
| EP | 2 000 115 A2 | 12/2008 |
| EP | 1994913 A3 | 12/2008 |
| EP | 1259193 B1 | 11/2010 |
| EP | 2266503 A2 | 12/2010 |
| EP | 2266504 A2 | 12/2010 |
| EP | 2266503 A3 | 4/2011 |
| EP | 2266504 A3 | 4/2011 |
| EP | 2364669 A2 | 9/2011 |
| EP | 1281375 B1 | 2/2012 |
| EP | 2364669 A3 | 3/2012 |
| ES | 2293734 T3 | 3/2008 |
| ES | 2313954 T3 | 3/2009 |
| ES | 2353733 T3 | 3/2011 |
| ES | 2381337 T3 | 5/2012 |
| FR | 2828263 A1 | 2/2003 |
| FR | 2828263 B1 | 5/2007 |
| GB | 2440809 A | 2/2008 |
| HK | 1053600 A1 | 7/2012 |
| JP | 2003-523262 T | 8/2003 |
| JP | 2003-524504 T | 8/2003 |
| JP | 2005-118585 A | 5/2005 |
| JP | 2007-296375 A | 11/2007 |
| JP | 2009-034529 A | 2/2009 |
| JP | 2009-061293 A | 3/2009 |
| PT | 1112042 E | 1/2008 |
| PT | 1259195 E | 12/2008 |
| PT | 1259193 E | 1/2011 |
| PT | 1281375 E | 3/2012 |
| WO | WO-90/09102 | 8/1990 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO-98/43556 | 10/1998 |
| WO | WO-98/46165 | 10/1998 |
| WO | WO-99/37337 | 7/1999 |
| WO | WO 99/42058 A1 | 8/1999 |
| WO | WO-99/66863 | 12/1999 |
| WO | WO 00/15148 A1 | 3/2000 |
| WO | WO 00/18333 A1 | 4/2000 |

(56) References Cited

FOREIGN PATENT DOCUMENTS

| | | |
|---|---|---|
| WO | WO-00/18445 | 4/2000 |
| WO | WO 2000/25702 A1 | 5/2000 |
| WO | WO 00/47139 A1 | 8/2000 |
| WO | WO-00/53125 | 9/2000 |
| WO | WO-00/62714 | 10/2000 |
| WO | WO 00/69367 A1 | 11/2000 |
| WO | WO-01/010209 A1 | 2/2001 |
| WO | WO 2001/35870 A1 | 5/2001 |
| WO | WO-01/41679 A1 | 6/2001 |
| WO | WO-01/51104 A1 | 7/2001 |
| WO | WO 01/54625 A1 | 8/2001 |
| WO | WO-01/58503 A1 | 8/2001 |
| WO | WO 01/62189 A1 | 8/2001 |
| WO | WO 01/64137 A1 | 9/2001 |
| WO | WO 2002/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO 2003/003949 A2 | 1/2003 |
| WO | WO-03/009785 A1 | 2/2003 |
| WO | WO 2003/011195 A2 | 2/2003 |
| WO | WO 2003/013239 | 2/2003 |
| WO | WO 03/028592 A1 | 4/2003 |
| WO | WO 03/032870 A1 | 4/2003 |
| WO | WO 03/047468 A1 | 6/2003 |
| WO | WO-03/079928 A2 | 10/2003 |
| WO | WO 2003/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/043301 A1 | 5/2004 |
| WO | WO 2004/082527 A2 | 9/2004 |
| WO | WO 2004/096100 A1 | 11/2004 |
| WO | WO 2005/021063 A2 | 3/2005 |
| WO | WO 2005/034812 A1 | 4/2005 |
| WO | WO 2005/062980 A | 7/2005 |
| WO | WO 2005/063980 A1 | 7/2005 |
| WO | WO-2005/072654 A1 | 8/2005 |
| WO | WO 2006/066327 | 6/2006 |
| WO | WO-2006/066327 A | 6/2006 |
| WO | WO 2006/076890 A1 | 7/2006 |
| WO | WO-2006/102063 A2 | 9/2006 |
| WO | WO 2006/108090 A2 | 10/2006 |
| WO | WO 2006/124649 A2 | 11/2006 |
| WO | WO-2006/124649 A2 | 11/2006 |
| WO | WO 2006/127756 A2 | 11/2006 |
| WO | WO 2006/127765 A1 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO 2007/059252 A1 | 5/2007 |
| WO | WO-2007/071436 A2 | 6/2007 |
| WO | WO 2007/120543 A1 | 10/2007 |
| WO | WO-2008/028569 A1 | 3/2008 |
| WO | WO 2008/045949 | 4/2008 |
| WO | WO 2008/070797 A2 | 6/2008 |
| WO | WO 2008/079962 A1 | 7/2008 |
| WO | WO 2008/101083 A2 | 8/2008 |

OTHER PUBLICATIONS

Translation of Aortenklappenbioprothese erfolgreich in der Entwicklung (2 pages), original German language document dated May 16, 2003.
Screen shots from http://www.fraunhofer.de/presse/filme/2006/index.jsp (2 pages), 2006.
Liang, Ma, et al., "Double-crowned valved stents for off-pump mitral valve replacement," European Journal of Cardio-Thoracic Surgery, 194-198 (5 pages), Jun. 13, 2005.
Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.
File history for German Patent DE 195 46 692 filed Dec. 14, 1995 and patented Jul. 11, 2002.
Office Action dated Jul. 15, 2005 from abandoned U.S. Appl. No. 10/210,085.
Office Action dated May 14, 2007 from abandoned U.S. Appl. No. 10/210,085.
Response to Office Action dated Nov. 1, 2005 from abandoned U.S. Appl. No. 10/210,085.
Office Action dated Nov. 19, 2010 from abandoned U.S. Appl. No. 12/138,983.
Office Action dated May 27, 2011 from patented U.S. Appl. No. 12/138,983.
Response to Office Action dated Feb. 22, 2011 from patented U.S. Appl. No. 12/138,983.
Response to Office Action dated Oct. 26, 2011 from patented U.S. Appl. No. 12/138,983.
Office Action dated Oct. 14, 2010 from patented U.S. Appl. No. 12/139,074.
Office Action dated May 26, 2011 from patented U.S. Appl. No. 12/139,074.
Response to Office Action dated Mar. 14, 2011 from patented U.S. Appl. No. 12/139,074.
Response to Office Action dated Oct. 14, 2011 from patented U.S. Appl. No. 12/139,074.
Amendment/Response to Restriction Requirement dated Feb. 22, 2011 from patented U.S. Appl. No. 12/407,342.
Office Action dated May 26, 2011 from patented U.S. Appl. No. 12/407,342.
Response to Office Action dated Sep. 26, 2011 from patented U.S. Appl. No. 12/407,342.
Search Report dated Oct. 15, 2003 from the European Patent Office for European Patent Application No. EP 02291953.4.
Search Report (Rapport De Recherche) from French Application No. FR 01 10444 (undated).
Office Action dated Mar. 23, 2010 from Canadian Patent Application No. 2,436,258.
Office Action dated Apr. 7, 2011 from Canadian Patent Application No. 2,436,258.
First Examination Report dated May 29, 2007 in European Application No. EP 02291953.4.
Second Examination Report dated Jan. 10, 2011 in European Application No. EP 02291953.4.
Extended Search Report (Rapport De Recherche Europeenne) dated Mar. 23, 2011 in European Application No. EP 10 01 2198.
Extended Search Report (Rapport De Recherche Europeenne) dated Mar. 23, 2011 in European Application No. EP 10 18 4842.
Office Action and Search Report dated Nov. 11, 2010 in Austrian Utility Model Application No. GM201/2008-7.
Office Action dated Sep. 25, 2008 in Finish Utility Model Application No. U20080117.
Office Action dated Jun. 13, 2008 in Danish Utility Model Application No. BA 2008 00058.
Office Action dated Nov. 16, 2012 from patented U.S. Appl. No. 13/279,800.
Response to Office Action dated Apr. 15, 2013 from patented U.S. Appl. No. 13/279,800.
Office Action dated Nov. 7, 2013 from patented U.S. Appl. No. 13/286,459.
Response to Office Action dated Apr. 8, 2013 from patented U.S. Appl. No. 13/286,459.
Office Action dated Nov. 20, 2014 from now abandoned U.S. Appl. No. 14/019,071.
English Translation of DE 19546692 A1 (4 pages), original German language document dated Jun. 19, 1997.
English Translation of DE 19857887 A1 (2 pages), original German language document dated Jun. 6, 2000.
Office Action dated Aug. 26, 2016 from co-pending U.S. Appl. No. 14/563,473.

DEVICES USEFUL FOR IMPLANTATION AT A HEART VALVE

STATEMENT OF RELATED APPLICATIONS

This application is a continuation under 35 U.S.C. § 120 of U.S. application Ser. No. 14/019,071, filed Sep. 5, 2013, now pending, which is a continuation under 35 U.S.C. § 120 of U.S. application Ser. No. 13/279,800, filed Oct. 24, 2011, now U.S. Pat. No. 8,585,756 B2, which is a continuation under 35 U.S.C. § 120 of U.S. application Ser. No. 12/138,983, filed on Jun. 13, 2008, now U.S. Pat. No. 8,216,301 B2, which is a continuation under 35 U.S.C. § 120 U.S. application Ser. No. 10/210,085, filed on Aug. 2, 2002, now abandoned, which applications are incorporated herein by reference in their entireties.

TECHNICAL FIELD

The current invention relates to an implant implantation unit and to a procedure for fitting the unit in a tubular element.

The problem at the origin of the invention concerns the implantation of heart valves. Until recently this necessitated open heart surgical operations, with stages such as stopping the heart, the implementation of extra bodily blood circulation and restarting the heart after the implantation of replacement heart valves. These surgical operations are difficult and delicate and present mortal risks related to operating shocks.

BACKGROUND

U.S. Pat. No. 5,824,063 thus describes a unit carrying replacement heart valves, the unit comprising a tubular implant in synthetic material carrying internally a replacement valve in natural material.

U.S. Pat. No. 5,855,601 and U.S. Pat. No. 5,868,783 describe new heart valve implantation methods, which offer the advantage of avoiding open heart surgery. These methods provide the implantation, by movement through the blood circulation system, of a heart valve replacement unit comprising a radially expandable intra-vascular cylinder carrying a biological valve internally. An inflatable part of a balloon catheter is placed inside the carrier cylinder and the implantation is done by introduction into a vein and movement as far as the failed valve using A catheter. A two dimensional image screen display allows the detection that the carrier cylinder has reached the required position and the cylinder is then dilated by inflating the balloon through the catheter and maintains its expanded shape. The balloon is then deflated and withdrawn with the catheter.

The carrier cylinder presents a sealed casing, which is thus forced against the artery wall, so as to avoid the blood flow bypassing the replacement valve.

However, when the aorta is involved this procedure is not applicable because the coronary arteries open close to the failed native valves, so that the carrier cylinder is likely to block them, provoking the death of the patient.

SUMMARY

The inventors of the present application have therefore thought of providing two corresponding openings in the wall of the carrier cylinder casing. However, so that these openings will be placed opposite the two coronaries, the position of the carrier cylinder in the aorta must be completely controlled. Monitoring on the screen allows the progress, or axial position, of the carrier cylinder to be checked, but the angular position will be neither visible nor controlled.

The applicants have therefore found a solution, described below, allowing the position of the carrier cylinder to be controlled.

They have therefore thought about the resolution of the more general problem of positioning an implant unit or transport vehicle in a tubular element with difficult access and for which imaging is insufficient or even impossible. The field of application could thus concern other fields than the medical, such as the petroleum or nuclear industries, for installing sensors, valves and other items. The scope of the present application must therefore not be considered as limited to the resolution of the original problem. In a more general way, the invention aims to allow, the placing, in a difficult to access location of a tubular element, of a unit intended to carry an implant, whatever the function of the implant.

To this end, the invention concerns in the first place a unit for the implantation in a determined position of a tubular element with a wall comprising a cavity, the unit being arranged to cooperate with means for driving the unit in the tubular element, a unit characterized by the fact that it comprises deformable feelers arranged so that, under the control of means for remote activation, it passes from a stowed to a deployed functional shape, to detect the cavity and position itself there with reference to the position of the cavity.

Thus, the unit can be made to advance blind and the feelers allow the automatic detection of the cavity and positioning at it.

The final required position can also be reached even through a contraction of the tubular element for example an access artery leading to an artery of larger diameter.

The invention also concerns a process, which is not surgical and without therapeutic aim, for implantation of the inventive unit, at a predetermined position in a tubular element presenting a wall comprising a cavity which procedure is characterized by the fact that a user inserts the unit through an open end of the tubular element he activates drive means to make the unit advance to a position before the determined position, he commands the feeler remote activation means and, with the advance continuing, he stops the action of the drive means when he detects a blockage of the advance, indicating that the feeler means are positioned in the cavity.

BRIEF DESCRIPTION OF THE DRAWINGS

The characteristics and advantages of the present invention will appear more clearly with the aid of the following description of a particular form of the realization of the inventive unit and a variant, as well as the procedure for using it, with reference to the attached drawing, in which.

DETAILED DESCRIPTION

Figure 1:
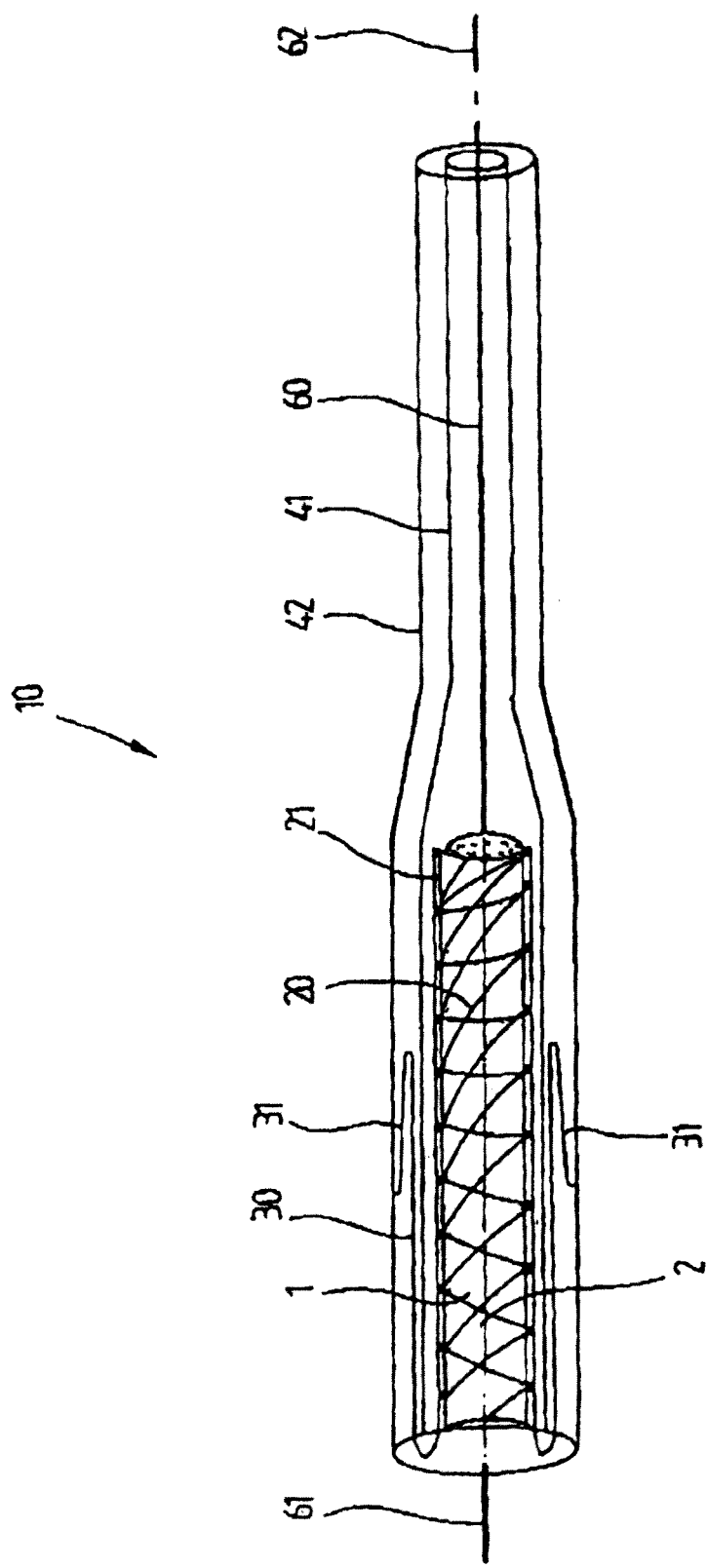
FIG. 1 is a lateral cross section of the inventive unit, representing the feeler positioning and anchoring elements, associated with a cylinder carrying a valve prosthesis, the whole being covered by two removable concentric activation casings, FIG. 2 corresponds to FIG. 1, the feeler positioning and anchoring elements having been deployed radially by axial withdrawal of the external casing, FIG. 3 corresponds to FIGS. 1 and 2, with the carrier cylinder surrounded by positioning and anchoring feeler elements having been deployed radially after axial withdrawal of the internal casing.

As shown in FIG. 1, the present implementation example corresponds to the medical problem, explained at the beginning, of implanting a functioning replacement valve for a native semilunar valve, such as the native aorta valve. The valve implantation unit 10 comprises a carrier element 20 to hold the implant, joined to a plurality of feeler, or palpitation, elements or fingers 30, 31, here regularly spaced angularly all around, for positioning and anchoring relative to relief features, specifically a cavity in the aorta wall, unit 10 being linked removably to a positioning catheter 60. Unit 10 is associated with two concentric sleeves 41, 42 for successive remote activation, by radial expansion, of feeler elements 30, 31 then the carrier element 20. The direction of movement of unit 10 is therefore towards the left in FIGS. 1 to 3. Reference 62 represents an axis of symmetry and the drive direction of unit 10 and catheter 60.

Figure 2:
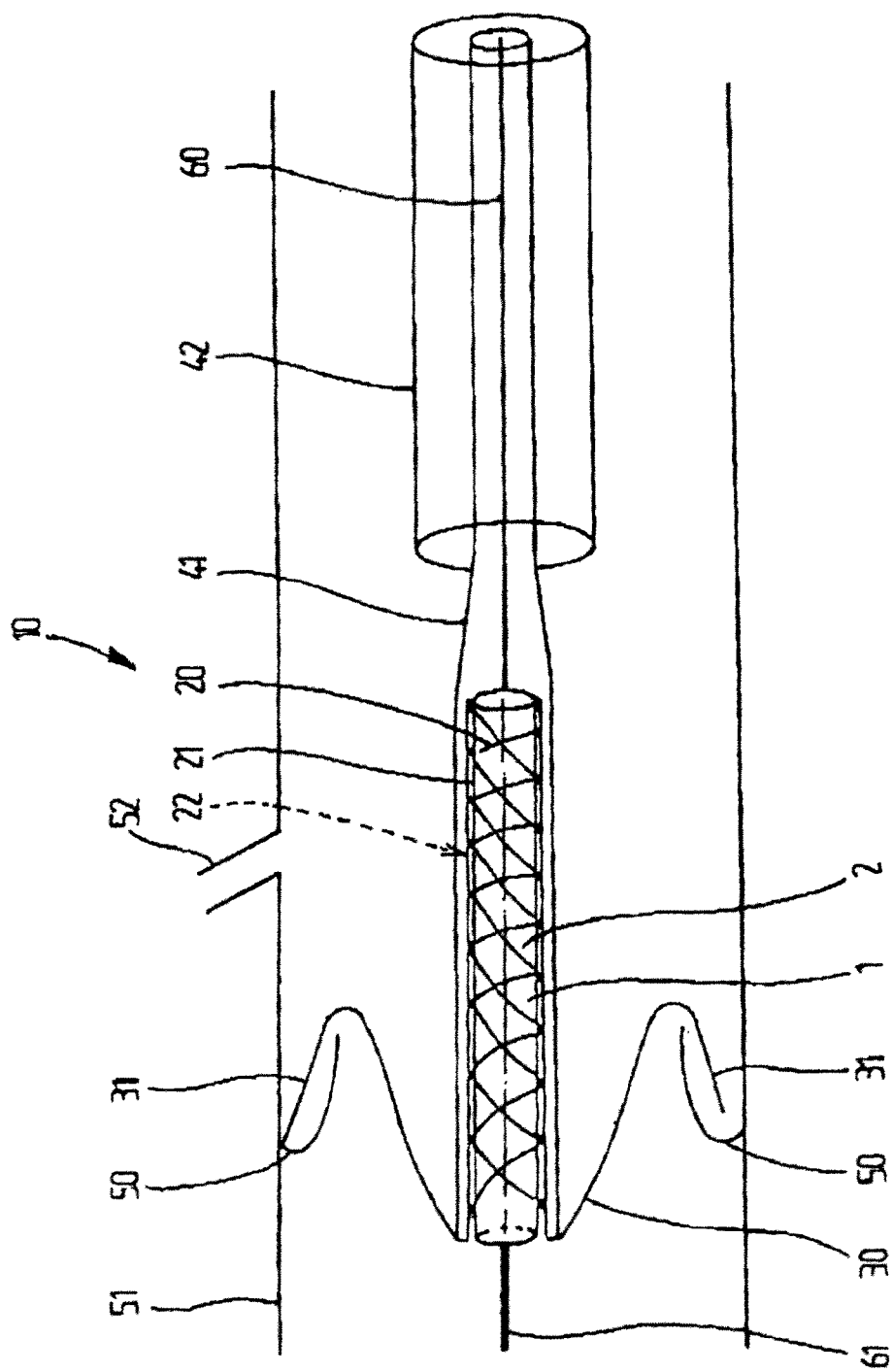

The implantation valve forms a prosthesis 1 comprising valve units 2 of the valve whose shape and size correspond perfectly, in the operating position, to those of the native aorta valves 50 (FIG. 2). The prosthesis 1 is fixed to the implant holding carrier vehicle element 20, here comprising a cylindrical mesh in a bio-compatible material such as steel, gold alloys and for preference as here, nitinol, which comprises a shape memory nickel-titanium alloy offering the ability to regain its shape after initial deformation, here by radial compression. The fixing of prosthesis 1 to the cylindrical nitinol mesh is made in well-defined locations leaving free those regions that correspond to the valve units 2 after deployment from the stowed position of FIG. 2, as illustrated below in respect of FIG. 3.

Figure 4:
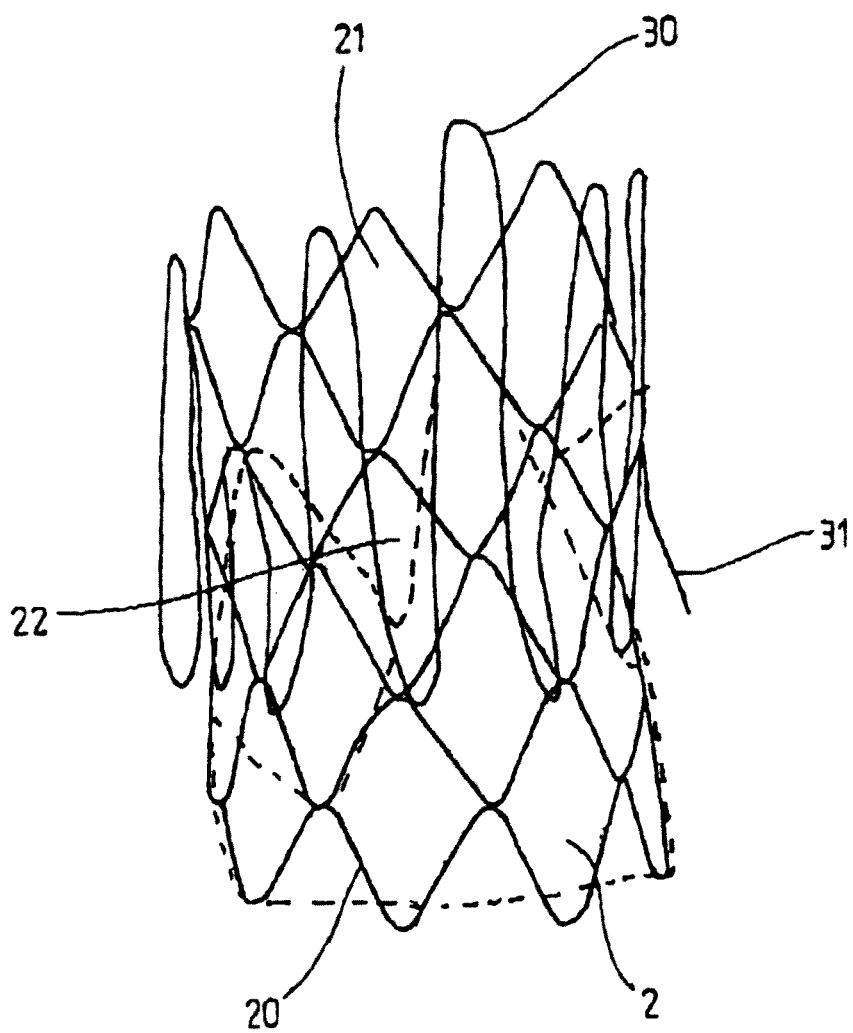
FIG. 4 is a lateral view of the carrier cylinder and the positioning and anchoring feeler elements.

FIG. 4 represents the cylindrical mesh 20 in the deployed form, carrying the valve units 2 also deployed internally, on which are connected the feeler elements 30, 31, here in the form of a generally cylindrical exterior ring of wire loops of which one (31) at least, here in fact three, protrudes laterally and towards the front, opposite the catheter 60. In this example, the loops 31 extend, in the deployed position, in a direction inclined at about 30 degrees towards the front (direction of movement towards the target position) relative to the axis 62 of the mesh 20 and the ring 30. The feeler elements 30, 31 are joined to the cylindrical mesh 20 in such a way that their axial and angular positions relative to it are perfectly defined. The assembly, cylindrical mesh 2 and feeler elements 30, 31, is here composed of the auto expandable bio-compatible material mentioned above.

The cylindrical carrier mesh 20 is here covered with an impermeable lateral casing intended to be pressed against the aorta wall to avoid bypassing by the blood circulation.

Figure 5:
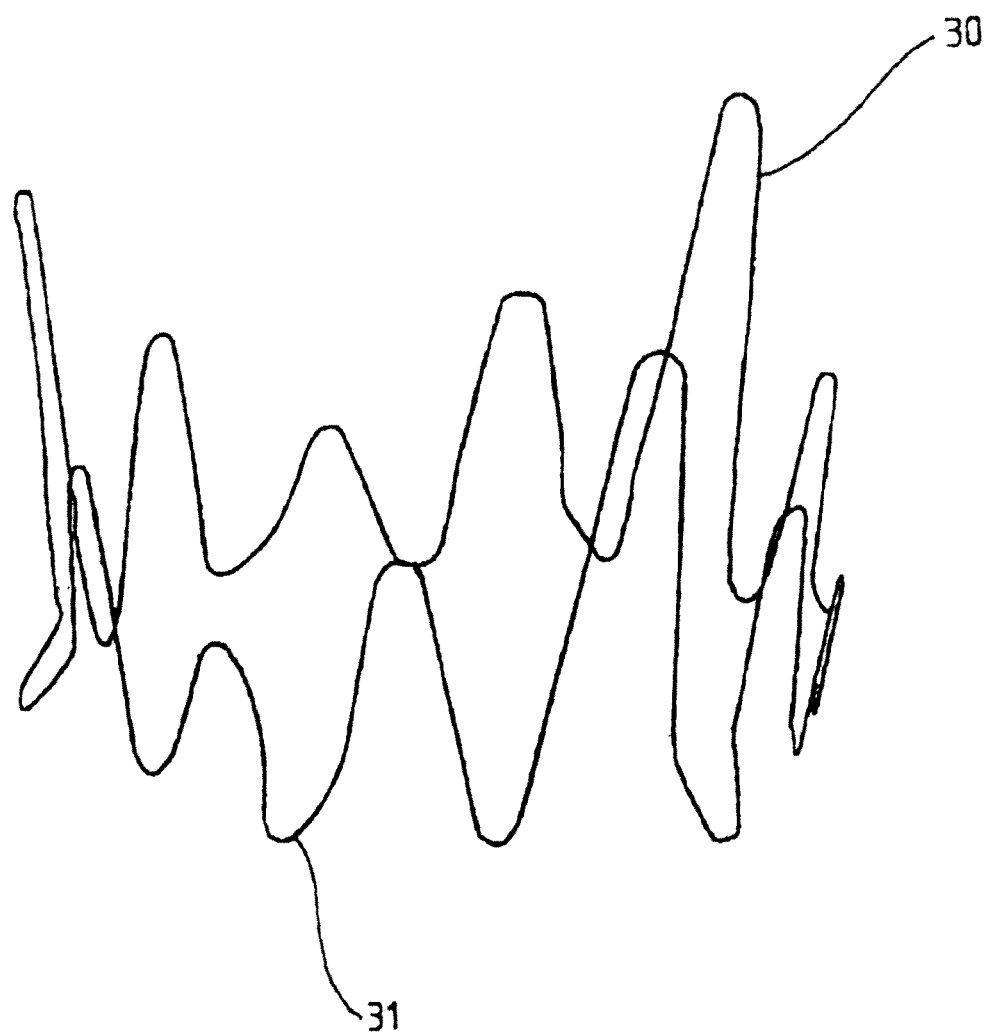
FIG. 5 is a lateral perspective view of the positioning and anchoring feeler elements.
Figure 6:
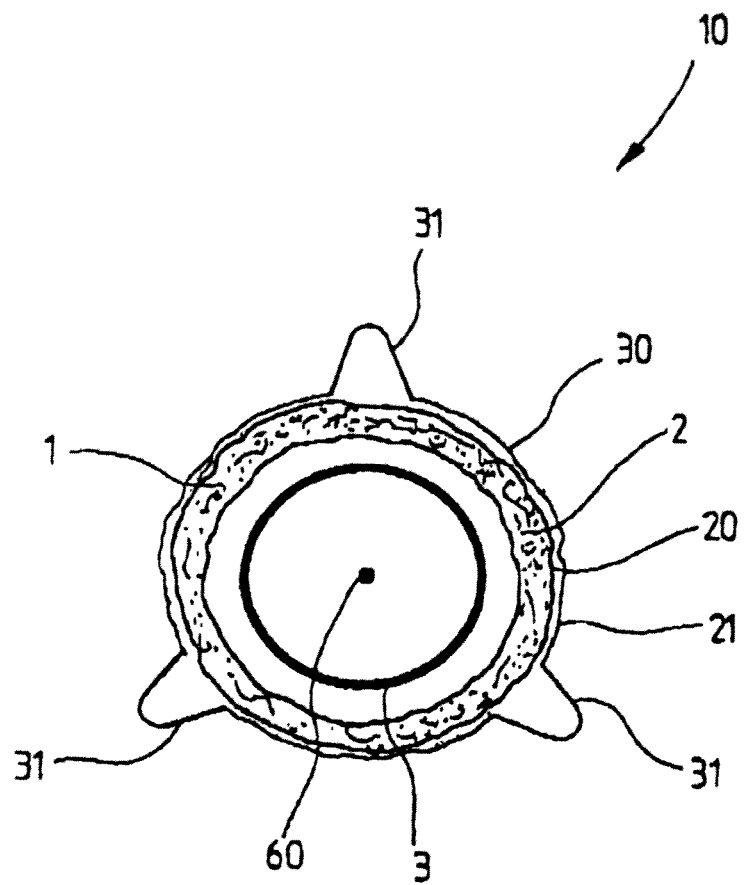
FIG. 6 is a schematic face view of the inventive unit.

FIG. 5 shows the feeler elements 30, 31 in perspective. FIG. 6 is a schematic view, along the unit 10 axial direction, showing the three loops 31 protruding laterally from the tubular grid 20 that carries them, while the 2 valve units of the valve to be implanted are fixed internally to the carrier cylinder 20.

In addition, if necessary, an inflatable balloon, joined to the catheter 60, can here be placed inside the carrier cylinder 20, to be fed with liquid under pressure through catheter pipe 60 so as to cause or assist the radial expansion of the carrier cylinder 20 to the required deployed form.

As the feeler elements 30, 31 are made in a self-expanding material such as nitinol, or an equivalent element forming an elastically protruding foot or finger, unit 10 is covered with an inhibition sleeve 42 to hold the feeler elements 30, 31 in a stowed position, the loops 31 being folded on the ring 30 and thus also on the mesh 20. Sleeve 42 extends to cover the catheter 60. A second sleeve 41, effectively the same length and without effect on the feeler elements 30, 31, is here similarly provided to hold the carrier cylinder 20 in the stowed position, so as to avoid unplanned deployment even in the absence of inflation of the balloon 3. The two sleeves 41, 42, are mounted concentrically on the catheter 60. The sleeves 41 and 42 are accessible from the end of catheter 60 opposite to the unit 10. Elements 3, 41, 42, and 60 comprise a functional catheter assembly separable from the unit 10, for the positioning and switching on this latter and the payload (2).

The two sleeves 41, 42 inhibit the radial deployment or the structure 20, 30, 31 until the latter reaches the region of the native aorta valve 50 to be functionally replaced, and thus allow the introduction of unit 10 into the blood circulation system, such as a reduced diameter incised artery. As indicated, the catheter 60, with balloon 3, is detachably joined to the implantation unit 10 so as to allow an axial advance of the implantation unit 10 in the blood circulation system up to the implantation location, and the withdrawal of the catheter assembly 3, 41, 42, 60.

To free itself, the catheter 60 comprises, in this example, at the fixed end of carrier cylinder 20, a spring effect clamp (not shown), with remotely controlled teeth, fitted to rotate radially, for connection to the unit 10 and has a sliding central remote control metal wire to axially push back the claw branches or teeth so as to separate them radially and so free the catheter 60 of the implantation unit 10 according to the sugar claw principle.

When the cylindrical mesh 20 is deployed, the pressure on the aorta internal wall is provided by the shape memory effect, which thus ensures the radial dilation of the prosthesis 1. The failed native valve unit 50 is flattened by being pressed by the tubular grid 20 against the aorta internal wall, each of the three loops 31 protruding laterally having previously been engaged in one, specifically, of the three native valve units 50 and being similarly pressed to confirm its anchorage. The valve units 50 are thus clamped between the mesh 20, 30 and the respective loops 31.

The implantation procedure for the unit 10 described above, according to the preferred method of implementation, comprises the following steps. After insertion of the implantation unit 10 into the circulatory system, and after having pushed it using the catheter 60 to a position above the final target position, here precisely where the unit 10 arrives in the aorta, and so that a large diameter space is thus offered to it, the following stage consists of freeing the lateral loops 31, initially pressed against the stowed mesh 20, 30. The release of the loops 31 is done by withdrawing the external retention sleeve 42 (FIG. 2), that is to say withdrawn whilst maintaining the thrust on the catheter 60. The forward movement of the unit 10 continuing, the loops 31, being then protruded laterally towards the front with respect to the axial direction of forward movement, in opposition to the catheter 60, they form a sort of tripod and simultaneously penetrate the three respective native valves 50, effectively identical, comprising an arrangement of connection pockets in a complete ring with each extending over 120 degrees, filling in total the whole of the perimeter of the aorta internal wall 51. Each native valve unit 50 offers a rounded base.

Each lateral protrusion 31, turned towards the front, presses against the base of the native valve unit 50 concerned, in general in a point distant from the "lowest" point of the base, that is to say, the furthest from the catheter 60. This is therefore a partial stop because the axial advance of the unit 10 continues by thrust from the catheter 60, the axial thrust of the unit 10 causing it to slide to the lowest point. The bottom of the valve unit 50 thus comprises a sort of inclined plane guidance track (not orthogonal to the axis (62) of the aorta) which, in reaction to the axial forward force, creates a circumferential reaction force causing the rotation of the unit 10 until the feeler loop considered 31 reaches the lowest point, which corresponds to a complete end wall (with tangential plane orthogonal to the axis (62) of the aorta 51), and thus corresponds to the final axial and angular position sought for the unit 10.

Each lateral protrusion 31, with rounded ends, here as a loop, so as to be able to slide in the bottom of the valve unit 50, thus comprises, by continuous cooperation with the variable depth rounded base of the native valves 50, means for rotational drive of the feeler elements 30, 31 and thus also of the cylindrical mesh 20, to which it is joined. However if the lateral protrusions 31 by chance bump against a native valve unit 50 commissure, the implantation unit 10 can be slightly withdrawn and the operator twists the catheter 60 so that it pivots angularly to be able to restart the positioning and anchoring operation.

The assembly, feeler elements 30, 31 and cylindrical mesh 20, being positioned axially and at an angle with respect to the specific relief of the aorta comprising the native valve units 50, it is then automatically positioned with respect to the two coronary openings (52) for which the axial and angular position with respect to the valve units 50 is determined and known, the valve unit-coronary axial distance evidently depending on the size of the patient.

In the case considered here in which the three native valves 50 form a circular circumference to the aorta wall extending over 360 degrees, a single lateral protrusion is sufficient to modulo 120 degrees positioning and anchoring the cylindrical mesh 20. As stated above, in a general case, there could only be one feeler 30, 31 working with a row of cavities or pockets covering all the circumference of the tubular element, or even a single pocket of cavity 50 only occupying a sector of the circumference and a plurality of feelers 30, 31 all around the unit 10 so that one of them fits in the cavity.

It will be noted that, in the present example, modulo 120 degrees positioning can be tolerated because the two coronaries (52) naturally effectively show this angle. If this was not the case, it would be necessary laterally to enlarge two openings or serrations 22 provided in the casing 21 so that they were positioned opposite the coronaries (52) (FIG. 4 and position marked on FIG. 3.), or again to feel, using the feelers 31, the coronaries (52) themselves, which also comprise cavities in the aorta 51, and not to sense the native valve units 50. This case corresponds to the variant described below.

Figure 3:
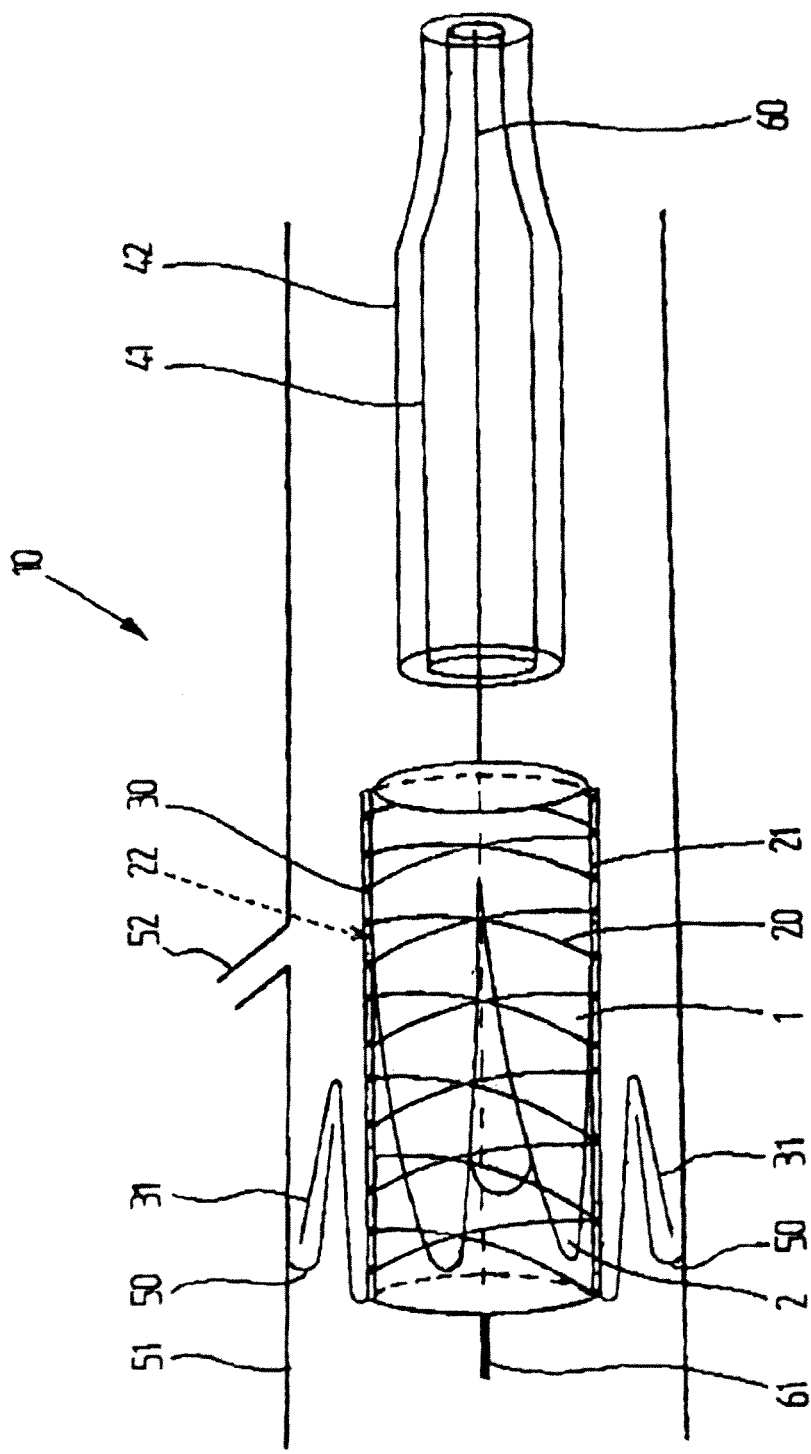

Positioning thus having been effected, the following stage, as show in FIG. 3, consists of deploying the cylindrical mesh 20 carrying internally the valve units 2 by withdrawing the internal retaining sleeve 41, to consolidate the anchorage and change the valve units 2 to their operational form. For the clarity of the drawing, in particular the protrusions 31, the mesh 20 has been represented with a relatively small diameter, whereas in fact it matches that of the aorta 51, with a slight increase to ensure the required lateral pressure. In the same way, two protrusions 31 have been represented, although in fact they are separated by 120 degrees, with the plane of FIG. 3 only in reality cutting one. For this reason, only a single coronary has been drawn (52).

The three loops 31 protruding however provide by themselves a basic anchorage in the bottom of the pockets comprising the native valves 50 and ensure the positional stability of the prosthesis 1. After a few weeks, fibrous tissue will cover the prosthesis 1, combining with the lateral protrusions 31 to further improve the fixing.

It will be noted however that, in the deployed position of the feeler elements 31, it is not necessary that their free ends should be firmly pressed against the aorta 51 wall. It is sufficient that their radial extension should be sufficient that they hook, in passing, onto the valve units 50. Because of this, when the feeler elements 31 are deployed, before the final position, the later axial translation of the unit 10, up to this position, is done without "hard" rubbing under pressure, of the part of the loops 31 on the aorta wall 51. The latter thus does not run any risk of damage due to scratching or piercing, the loops 31 being feelers, that follow the aorta wall 51 to detect the valve units 50. As described above, rounded feet or lugs can also be suitable.

The feeler loops 31 thus do not here have very firm anchoring of the unit 10 in the aorta 51 as their main function, because they do not aim to exert a large radial anchoring pressure. As indicated above, this is only a basic anchoring. It is then the radial deployment of the mesh 20 that creates, by shape memory, a definitive radial anchoring pressure that forces the mesh 20 under pressure against the aorta wall 51 and thus blocks any relative movement, such as the withdrawal of the unit 10 that could be due to blood flow, in a direction opposite to the insertion of the unit 10. The feeler elements 11 are then functionally superfluous. They however contribute to maintaining position by pinching the valve units 2. As the mesh offers a relatively high contact surface with the aorta 51, any risk of damaging the latter is excluded. The shape memory material allows the radial pressure exerted on the aorta 51 to be precisely determined, the diameter of the latter thus increased being then perfectly defined, which eliminates all risk of excessive radial stress.

The inventive procedure can be implemented in non-surgical manner and without therapeutic aims, to implant the unit 10 (or equivalent) in a determined position in a tubular elements offering a wall including a cavity, the procedure comprising the following stages: a user inserts the unit (10) into an open end to the tubular element, the user activates the drive means (60) (catheter, external magnet or other) to move the unit (10) up to a position upstream the determined position, the user commands the feeler element (30,31) activation means (42) and, the forward motion continuing, the user stops the activation of the drive means (60) when he detects a blockage of the advance, due to the fact that the feeler means (30,31) are positioned in the cavity.

To ease the drive of the unit 10, this one can be associated with a type of precursor rostrum 61 (FIGS. 1 to 3) forming a guide, in the form of a cylindrical element of a limited diameter, joined to the catheter 60.

It will be noted that the implantation unit according to the invention can, first, be implanted alone, without implant or payload, the latter being implanted later on the implantation unit according to the same principle. In a similar case, the inventive unit comprises means for receiving the second support, to come, of the implant, said means being arranged to ensure the positioning and anchorage, both axially, by stopping, and radially, with angular error correction means such as a finger or cavity provided to fit with an element of matching shape in the second support.

Figure 7:
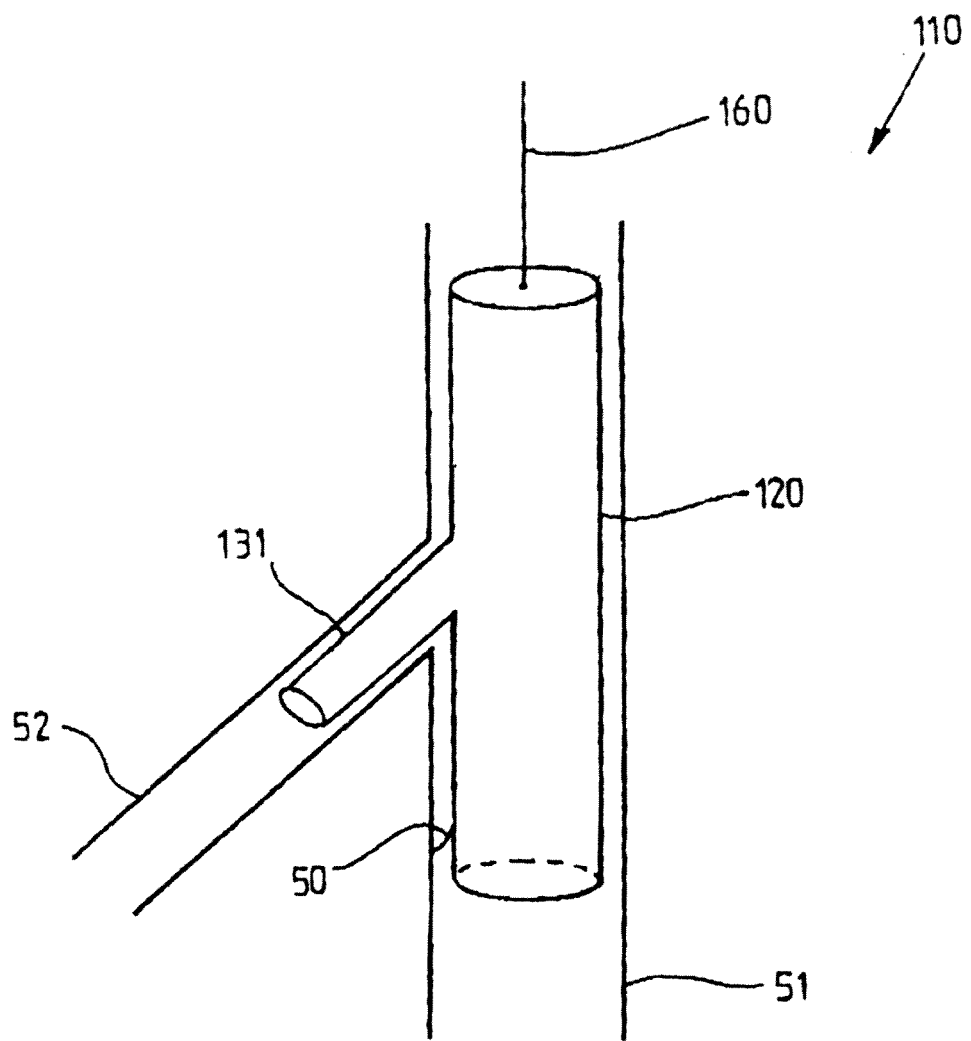
FIG. 7 is a schematic lateral section of the variant.

In the variant shown in FIG. 7, the implantation unit has the reference 110 and comprises functional elements similar to those of unit 10, with the same references preceded by the hundred 1, which have not however all been represented, with the aim of clarity. The cylindrical carrier element 120 is joined to a feeler element 131 which protrudes laterally and which has the same type of construction as the carrier element 120. In precise fashion, the feeler element 131 appears in the form of a cylinder, stowed radially in the rest position. When the unit 110 is pushed by the catheter 160, towards the bottom in FIG. 7, from a position above that shown, it engages in the coronary 52 when the free end is thus released from contact with the internal wall of the aorta 51.

The unit 110 thus comprises a type of fork that locks by stopping in the bifurcation between the aorta 51 and the coronary 52. When the end position is reached the two cylindrical elements 120, 131 are deployed by two balloons respectively and form a type of two fingered glove.

Thus, during the positioning phase, the feeler 131 presents a radially stowed form, thus with reduced diameter not risking blocking the coronary 52. Then the feeler 131 is deployed, by inflation of the associated remote control balloon, and constitutes a lining, or internal 'casing', pressed against the internal wall of the coronary 52 in accordance with the principle explained above for the carrier cylinder 20.

It will be noted that, as 120 and 131 each occupy a particular branch 51, 52, they can be considered as functionally equivalent, with the two principle functions if required. Each of them can in effect be a payload (2) carrier and can also be considered as being a feeler, because the aorta 51 can be considered (functionally in the context of the present invention) as being a cavity or branch with respect to the coronary 52. Thus the feeler means comprise a cylindrical element 131 arranged to change from a stowed form to a radially deployed form, supported against a wall of the cavity, here the coronary 52, under the influence of remote control means (balloon and catheter 160), To avoid the risks of movement of the feeler 131 into the coupling position to the coronary 52, due to an angular error that necessitates several attempts, it can be arranged for a guide wire to be passed into the coronary 52 and the upper part of the aorta 51, the unit 110 being threaded above it across the feeler 131 that is thus angularly oriented towards the coronary 52. Another guide wire can at the same time guide cylinder 120 into the aorta 51.

What is claimed is:

1. A prosthesis for implantation at a native semilunar valve site of a subject, the valve site having three semilunar sinuses and three native commissures, the prosthesis comprising:
    a valve prosthesis support structure comprising:
        a carrier structure configured to carry prosthetic valve leaflets, and
        exactly three engagement arms that meet one another at three respective junctures, wherein the engagement arms are shaped so as to define three peak complexes at the three respective junctures, and three trough complexes, each of which is between two of the peak complexes,
    wherein in an implanted position of the prosthesis:
        each of the engagement arms is configured to be at least partially disposed within a respective one of the semilunar sinuses, such that each of the peak complexes is disposed distal to a respective one of the native commissures, and each of the trough complexes is disposed at least partially within the respective one of the semilunar sinuses, and
        the prosthesis is configured such that the native valve leaflets are configured to be positioned between the carrier structure and the engagement arms.

2. The prosthesis according to claim 1, wherein:
the prosthesis is configured to be implanted at a native aortic valve site of the subject, the semilunar sinuses including respective aortic sinuses; and
in the implanted position of the prosthesis, each of the engagement arms is configured to be at least partially disposed within the respective one of the aortic sinuses.

3. The prosthesis according to claim 1, wherein:
the native semilunar valve has native leaflet roots and transitions between the semilunar sinuses; and
the engagement arms are configured to contact respective transitions between the respective semilunar sinuses and respective native leaflet roots of the native valve complex during implantation of the prosthesis.

4. The prosthesis according to claim 1, wherein, in said implanted position, the prosthesis is configured to apply a radial force outwardly against the native semilunar valve.

5. The prosthesis according to claim 1, wherein the prosthesis is configured, upon implantation thereof at the native semilunar valve site, to embrace leaflets of the native semilunar valve.

6. The prosthesis according to claim 1, wherein the prosthesis is configured such that, upon implantation at the native semilunar valve site, the engagement arms are alignable with respective ones of the semilunar sinuses by rotation of the prosthesis.

7. The prosthesis according to claim 1, wherein each of the engagement arms is configured to engage a respective one of the semilunar sinuses upon implantation of the prosthesis.

8. The prosthesis according to claim 1, wherein:
the prosthesis defines a longitudinal axis; and
each of the engagement arms is shaped to define a length, parallel to the prosthesis longitudinal axis, between (a) at least one of the junctures and (b) a contact point of one of the engagement arms that is configured to meet at the juncture with a sinus floor of the respective one of the semilunar sinuses upon implantation of the prosthesis, which length is greater than a distance of a native valve leaflet sinus to a free end of the native valve leaflet.

9. The prosthesis according to claim 1, wherein:
the prosthesis comprises a prosthetic valve comprising one or more prosthetic leaflets; and
at least a portion of each of the prosthetic leaflets is configured to assume a closed position during diastole and an open position during systole.

10. The prosthesis according to claim 9, wherein at least the portion of the prosthetic leaflets is not directly coupled to any of the engagement arms.

11. The prosthesis according to claim 9, wherein:
the prosthesis defines a longitudinal axis; and
the prosthetic valve is coupled to the support structure such that at least a portion of a length of the prosthetic leaflets parallel to said longitudinal axis is configured to be positioned distal to native valve leaflets of the native semilunar valve, upon implantation of the prosthesis.

12. A prosthesis for implantation at a native valve site, the prosthesis comprising:
- a fixation member configured to be positioned at least partially downstream of the native valve, the fixation member comprising:
  - a plurality of leaflet engagement arms configured to contact respective downstream sides of leaflets of the native valve in an implantation position of the prosthesis, the plurality of leaflet engagement arms being configured to apply a first force to tissue of the native valve in the implantation position,
  - a carrier element configured to contact an upstream side of leaflets of the native valve in the implantation position of the prosthesis, the carrier element being configured to apply a second force to tissue of the native valve in the implantation position of the prosthesis,
  - wherein the prosthesis is configured to be anchored in the implantation position at the native valve site via application of the first and second forces, and
  - wherein the leaflet engagement arms and the carrier element are configured to capture leaflets of the native valve therebetween in the implantation position of the prosthesis; and
- prosthetic valve leaflets supported within and coupled to the carrier element.

13. The prosthesis of claim 12, wherein the prosthesis is configured to embrace, without clamping, leaflets of the native valve during implantation of the prosthesis.

14. The prosthesis of claim 12, wherein the prosthesis is configured to be implanted at a semilunar valve site.

15. The prosthesis of claim 12, wherein:
- the prosthesis is configured to be implanted at a native valve site comprising three leaflets and three commissures; and
- the plurality of leaflet engagement arms comprises three leaflet engagement arms.

16. The prosthesis of claim 12, wherein the plurality of leaflet engagement arms are spaced from each other by gaps therebetween such that, in the implantation position of the prosthesis, the leaflet engagement arms are configured to be respectively rotationally aligned with the leaflets of the native valve and the gaps between the leaflet engagement arms are configured to be respectively rotationally aligned with commissures of the native valve.

17. The prosthesis of claim 12, wherein the fixation member is self-expandable.

18. The prosthesis of claim 12, wherein the prosthetic valve leaflets are biological valve leaflets.

19. The prosthesis of claim 12, wherein the plurality of leaflet engagement arms comprises a number of leaflet engagement arms equal to a number of the prosthetic valve leaflets.

20. The prosthesis of claim 12, wherein the prosthesis is configured to be implanted in an endovascular procedure.

21. The prosthesis of claim 12, wherein the second force comprises a radial outwardly directed force.

22. A prosthesis for implantation at a native semilunar valve site of a subject, the prosthesis comprising:
- a valve prosthesis support structure comprising:
  - a tubular carrier element configured to support a valve prosthesis; and
  - exactly three engagement arms that meet one another at three respective junctures, the three engagement arms being shaped so as to define three peak complexes at the three respective junctures, and to define three trough complexes, each trough complex being located between two of the peak complexes;
  - wherein the engagement arms are positioned at respective angular locations around the tubular carrier element, at least a portion of each engagement arm being positioned radially outwardly of the tubular carrier element.

* * * * *